US008267963B2

(12) United States Patent
Williams

(10) Patent No.: US 8,267,963 B2
(45) Date of Patent: Sep. 18, 2012

(54) SUTURE ANCHOR LOADING DEVICE

(75) Inventor: Michael L. Williams, Clemmons, NC (US)

(73) Assignee: Cook Medical Technologies LLC, Bloomington, IN (US)

( * ) Notice: Subject to any disclaimer, the term of this patent is extended or adjusted under 35 U.S.C. 154(b) by 288 days.

(21) Appl. No.: 12/759,492

(22) Filed: Apr. 13, 2010

(65) Prior Publication Data

US 2010/0268274 A1 Oct. 21, 2010

Related U.S. Application Data

(60) Provisional application No. 61/170,438, filed on Apr. 17, 2009.

(51) Int. Cl.
 *A61B 17/04* (2006.01)
(52) U.S. Cl. ..................................... 606/232
(58) Field of Classification Search ............... 606/131, 606/139, 144–150, 157, 158, 210, 213, 225, 606/227, 232; 24/115 R, 129 R; 206/63.3, 206/438; 251/4, 9, 10
See application file for complete search history.

(56) References Cited

U.S. PATENT DOCUMENTS

| | | | | |
|---|---|---|---|---|
| 3,103,666 A * | 9/1963 | Bone | ................... | 227/67 |
| 5,085,661 A * | 2/1992 | Moss | ................... | 606/139 |
| 5,307,924 A * | 5/1994 | Manosalva et al. | ......... | 206/63.3 |
| 5,341,823 A * | 8/1994 | Manosalva et al. | ......... | 128/898 |
| 5,531,678 A * | 7/1996 | Tomba et al. | .............. | 606/142 |
| 5,531,699 A * | 7/1996 | Tomba et al. | .......... | 604/170.02 |
| 5,601,571 A * | 2/1997 | Moss | ................... | 606/139 |
| 5,647,874 A * | 7/1997 | Hayhurst | ................ | 606/232 |
| 2002/0087178 A1* | 7/2002 | Nobles et al. | ............. | 606/167 |
| 2004/0073233 A1* | 4/2004 | Jannot | .................. | 606/148 |

* cited by examiner

*Primary Examiner* — Ryan Severson
*Assistant Examiner* — David Eastwood
(74) *Attorney, Agent, or Firm* — Brinks Hofer Gilson & Lione

(57) ABSTRACT

A suture anchor member manual loading device may include a body comprising first and second portions preventing operator contact with a tip of a needle. An anchor receiving portion shaped to receive and restrain a suture anchor member is disposed in the first portion of the body. A suture receiving portion has a first end connected to the anchor receiving portion and a second end disposed on an outer surface of the body such that the suture receiving portion extends away from the anchor receiving portion at a non-parallel angle. When the suture is tensioned the anchor member is translationally and rotationally restrained against the anchor receiving portion. A needle receiving portion disposed in the second portion of the body is shaped to receive the needle such that the suture anchor member is received into a lumen of the needle when the needle is advanced through the needle receiving portion.

17 Claims, 13 Drawing Sheets

SUTURE ANCHOR LOADING DEVICE

RELATED APPLICATION

The present application claims the benefit of U.S. Provisional Application No. 61/170,438, filed on Apr. 17, 2009, the entirety of which is hereby incorporated by reference.

BACKGROUND

1. Field of the Invention

The present invention relates generally to visceral anchors for connecting a suture to tissue, and more particularly relates to a device used to load visceral anchors structures into an introducer.

2. Technical Background

Perforations in bodily walls may be naturally occurring, or formed intentionally or unintentionally. In order to permanently close these perforations and allow the tissue to properly heal, numerous medical devices and methods have been developed employing sutures, adhesives, clips, staples and the like. One class of such devices is commonly referred to as tissue anchors, T-anchors or visceral anchors. Exemplary tissue anchors are disclosed in U.S. Pat. No. 5,123,914, the entire contents of which are incorporated by reference herein.

Tissue anchors typically include a crossbar or some kind of anchoring member connected to a suture. The anchoring member and suture may take many forms. Generally, the suture and anchoring member are housed within a hollow distal tip of a needle. The needle is commonly housed within a delivery catheter or sheath to facilitate delivery and deployment of the needle at a desired treatment site within a patient. Once the delivery catheter has been advanced to the treatment site, the needle is used to pierce tissue and deliver the anchoring member on one side of the tissue, thereby leaving the suture extending through the aperture created by the needle back to the other side of the tissue. In some procedures, upon deployment of the anchoring members, the sutures of one or more tissue anchors may be collected and connected together, such as through tying the sutures together.

Typically, the anchoring members are loaded into the needle by hand either during manufacturing or by a physician at the time of use, thereby exposing the operator to the sharp needle and potential infection in the event a contaminated needle is reloaded during use. Therefore, it has become apparent to the inventor that an improved method and device for loading anchoring members without exposing the operator to the sharp needle and potential infection is desirable.

SUMMARY

Suture anchor loading devices are described which may protect an operator from coming in contact with a sharp tip of a needle when manually loading a suture anchor member into the needle. The invention may include any of the following aspects in various combinations and may also include any other aspect described below in the written description or in the attached drawings.

In one aspect, a suture anchor member loading device may include an anchor loading body having first and second portions shaped to prevent operator contact with a tip of a needle when manually loading a suture anchor member into the needle. An anchor receiving portion may be disposed in the first portion of the body and the anchor receiving portion may be shaped to receive and restrain a suture anchor member. A suture receiving portion may also be disposed in the first portion of the body. The suture receiving portion may have a first end in mechanical communication with the anchor receiving portion and a second end disposed on an outer surface of the body. In a one embodiment, the suture receiving portion may extend away from the anchor receiving portion at an angle. The suture receiving portion may be shaped to receive a suture that is connected to the suture anchor member such that when the suture is tensioned, the suture anchor member is translationally and rotationally restrained against the anchor receiving portion.

The suture anchor member loading device may also include a needle receiving portion disposed in the second portion of the body. The needle receiving portion may be shaped to receive and slidably restrain the needle such that when the needle is slidably advanced through the needle receiving portion, the suture anchor member is received into a lumen of the needle.

In another aspect, the anchor receiving portion, the suture receiving portion, and the needle receiving portion may be slots that extend from an outer surface of the anchor loading body toward a center portion thereof. In one embodiment, the suture receiving portion is a slit extending from an outer surface of the body toward a center of the body, the slit having opposing portions which engage each other when no suture is disposed within the slit, and which engage and frictionally secure the suture when the suture is disposed within the slit and between the opposing portions. In one aspect, the needle receiving portion and the anchor receiving portion may be substantially coaxial.

In another aspect, the anchor member receiving portion may be a slot having a first width at an outer portion thereof, and a second width at an inner portion thereof. The second width is greater than the first width. In one embodiment, the needle receiving portion and the anchor member receiving portion are connected to each other, and the first and second widths of the anchor member receiving slot are substantially the same as the first and second widths of the needle receiving slot, respectively, such that the anchor member receiving slot and the needle receiving slot form a single substantially continuous slot having substantially the same shape.

In another embodiment, the first portion of the body and the second portion of the body are connected by a hinge member. The body may have a first configuration where the first and second portions are displaced from each other, and a second configuration wherein the first and second portions are rotated toward each other about the hinge member such that the anchor receiving portion is disposed adjacent the needle receiving portion, thereby allowing the suture anchor member to be inserted into the lumen of the needle when the needle is slidably advanced through the needle receiving portion. The hinge member may be a flexible member integrally formed with the first portion at a first end and with the second portion at a second end. In one aspect, the anchor receiving portion may include a needle alignment member that protrudes away from an outer surface thereof. The needle alignment member may be shaped to engage and align the needle when the needle is advanced through the needle receiving section.

In one aspect, a kit may be provided including a suture anchor member loading device having an anchor loading body with first and second portions shaped to prevent operator contact with a tip of a needle when manually loading a suture anchor member into the needle. An anchor receiving portion may be disposed in the first portion of the body and the anchor receiving portion may be shaped to receive and restrain a suture anchor member. A suture receiving portion may also be disposed in the first portion of the body. The suture receiving portion may have a first end in mechanical communication with the anchor receiving portion and a second end disposed on an outer surface of the body. The suture receiving portion extends away from the anchor receiving portion at an angle and may be shaped to receive a suture that is connected to the suture anchor member such that when the suture is tensioned, the suture anchor member is translationally and rotationally restrained against the anchor receiving portion. A needle receiving portion is disposed in the second portion of the body and is shaped to receive and slidably restrain the needle such that when the needle is slidably advanced through the needle receiving portion, the suture anchor member is received into a lumen of the needle.

The kit also includes at least one suture anchor member attached to a first end of a suture and a delivery needle. The delivery needle may include a sharp distal end, a lumen extending along a central axis of the needle, and a slot disposed at the sharp distal end. The lumen may be sized to slidably receive the suture anchor member, and the slot may extend proximally from a distal portion of the sharp distal end. The slot may be shaped to receive a portion of the suture. A sheath having a lumen sized to slidably receive the delivery needle is also included. The sheath may include a slit disposed at a distal end of the sheath, with the slit having opposing portions which engage each other when no suture is disposed within the slit, and which engage and frictionally secure the suture when the suture is disposed within the slit and between the opposing portions. Packaging may also be included that removably secures the suture anchor member, suture, the suture anchor member loading device, the delivery needle and the sheath.

A method of manually loading a suture anchor member into a needle may include: providing an anchor loading body shaped to prevent operator contact with a tip of a needle when a suture anchor member is manually loaded into the needle; inserting an anchor member attached to a suture into an anchor member receiving portion disposed in a first portion of the anchor loading body, the anchor member receiving portion being shaped to receive the anchor member; slidingly advancing the anchor member along the anchor member receiving portion until the suture is substantially aligned with a suture receiving portion in angular communication with the anchor member receiving portion; placing the suture within the suture receiving portion; causing the anchor member to engage a portion of the anchor member receiving portion by tensioning the suture, the anchor member thereby being restrained against the anchor member receiving portion; inserting the needle into the needle receiving portion; slidingly advancing the needle until the needle contacts the anchor member; manipulating the needle such that an end of the anchor portion is received into a tip of the needle; and advancing the needle until substantially the entirety of the anchor member is housed within a lumen of the needle.

Another method of manually loading a suture anchor member into a needle may include: providing an anchor loading body having first and second portions, the anchor loading body being shaped to prevent operator contact with a tip of a needle when a suture anchor member is loaded into the needle, wherein the first portion and the second portion are rotatably connected by a hinge member; placing an anchor member attached to a suture in an anchor member receiving portion that is disposed in a first portion of the anchor loading body such that the suture is substantially aligned with a suture receiving portion in angular mechanical communication with the anchor member receiving portion, the anchor member receiving portion being shaped to receive the anchor member; placing the suture within the suture receiving portion; causing the anchor member to engage a portion of the anchor member receiving portion by tensioning the suture, the anchor member thereby being restrained against the anchor member receiving portion; inserting the needle into the needle receiving portion; rotating the first portion toward the second portion about the hinge member such that the anchor member is adjacent the needle receiving portion; slidingly advancing the needle between the anchor receiving portion and the needle receiving portion until the needle contacts the anchor member; manipulating the needle such that an end of the anchor portion is received into a tip of the needle; and advancing the needle until substantially the entirety of the anchor member is housed within a lumen of the needle.

The foregoing paragraphs have been provided by way of general introduction, and are not intended to limit the scope of the following claims. The presently preferred embodiments, together with further advantages, will be best understood by reference to the following detailed description taken in conjunction with the accompanying drawings.

BRIEF DESCRIPTION OF THE DRAWINGS

The invention may be more fully understood by reading the following description in conjunction with the drawings, in which.

DETAILED DESCRIPTION

Referring now to the figures, FIGS. 1-5b illustrate a device for loading a suture anchor member into a needle according to an embodiment of the present invention. While the following description is directed to inserting suture anchor members into a needle, it should be understood that the invention is not limited thereto, and may be utilized to load suture anchor members into a cannula or any receiving structure having sharp edges or structures that have been contaminated and may injure or expose an operator to harmful pathogens through contact therewith. Exemplary needle and delivery system anchors are disclosed in U.S. Pat. No. 5,123,914, and U.S. patent application Ser. No. 11/946,565, the entirety of which are incorporated by reference herein.

Figure 5A:
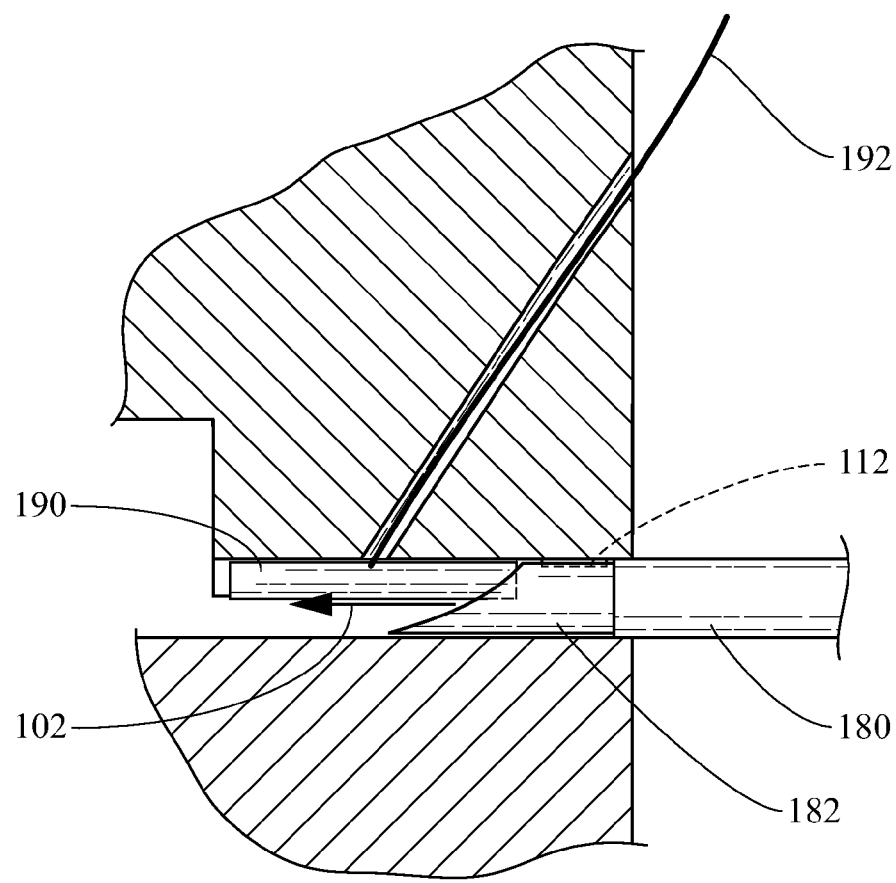
FIG. 5a is a side cross sectional view of the embodiment of FIG. 4 in the anchor member insertion configuration.
Figure 5B:
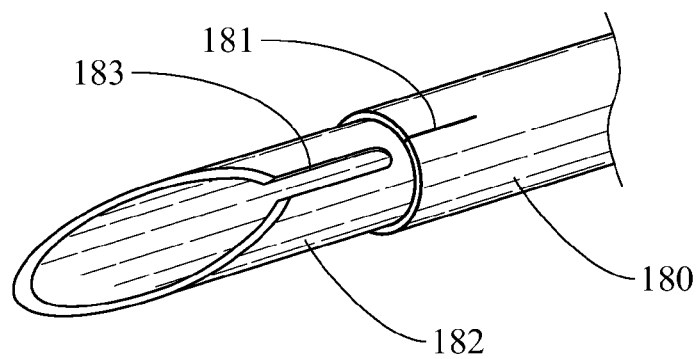
FIG. 5b is a perspective view of a needle housed within a delivery catheter.

For example, as shown in FIG. 5b, a needle 182 may define a lumen and a longitudinal axis of a medical system comprising the needle 182 and a sheath 180 disposed therearound. The needle 182 may be constructed of a metal or alloy such as stainless steel or nitinol, although other metals, alloys and polymers can be used for the needle 182, as is known in the art. The needle lumen is sized to slidably receive the suture anchor member 190 therein. In particular, the suture anchor member 190 generally comprises an anchoring structure and a suture 192 attached thereto. The suture anchor member 190 is received within the needle lumen along with a portion of the suture 192. A distal end comprising a sharp tip of the needle 182 also defines a slot 183 that is longitudinally extending and that opens longitudinally at the distal end of the needle 182. The slot 183 may be sized to receive the suture 192 therein. It should be understood that the needle 182 may or may not include the slot 183, although it is preferable to keep the suture 192 safe from the sharp distal tip of the needle 182 through provision of the slot 183.

The sheath 180 defines a sheath lumen which is sized to slidably receive the needle 182 therein. The sheath 180 may be formed of a plastic such as polytetrafluoroethylene (PTFE), expanded polytetrafluoroethylene (EPTFE), polyethylene ether ketone (PEEK), polyvinylchloride (PVC), polycarbonate (PC), polyamide including nylon, polyimide, polyurethane, polyethylene (high, medium or low density), or elastomers such as Santoprene®, including multi-layer or single layer constructions with or without reinforcement wires, coils or filaments. A suture retention slit 181 may be formed in a distal end of the sheath 180. In operation, once the suture anchor member 190 is loaded into the distal end of the needle 182, the suture 192 is pulled in the proximal direction, thereby tensioning the suture anchor member against the needle 182/slot 183. The suture is then inserted into the suture retention slit 181, thereby frictionally securing the suture 192 and preventing the suture anchor member 190 from inadvertently becoming dislodged from the needle 182.

Figure 1:
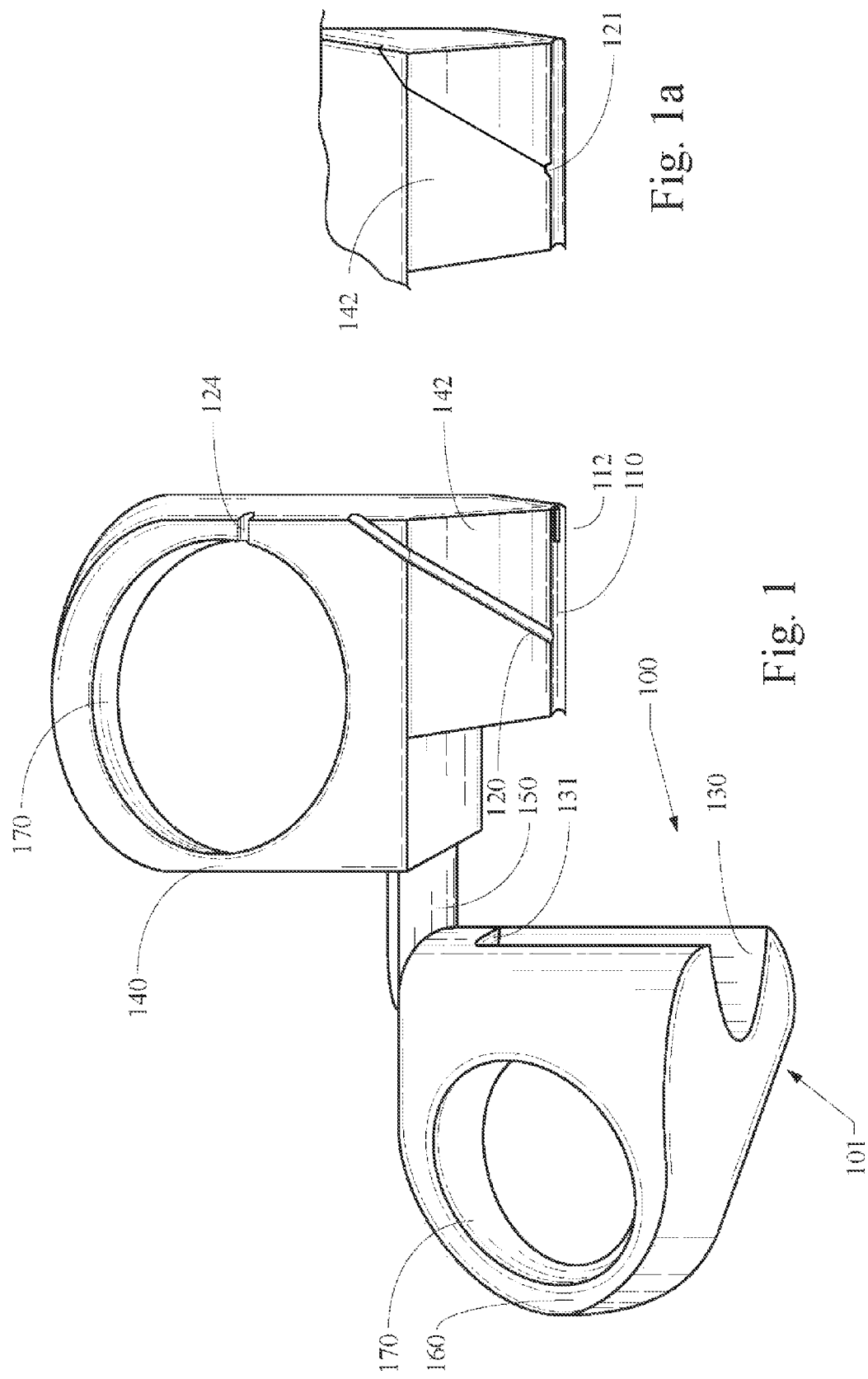
FIG. 1 is a perspective view of an embodiment of a suture anchor member loading device in an initial configuration.

Turning to FIG. 1, the suture anchor member loading device 100 includes a body 101 having a first portion 140 and a second portion 160. The first portion includes a main body that may be substantially "D" shaped and includes an operator interface feature 170 in the form of an aperture that is sized to receive a human finger. The main body also includes a lock notch 124 disposed on an upper portion of the main body. The lock notch 124 has a tapered, "V"-like shape that is sized to receive and frictionally secure a suture when it is inserted into the open, wide portion of the notch 124 and advanced toward the narrow closed portion thereof.

Figure 2:
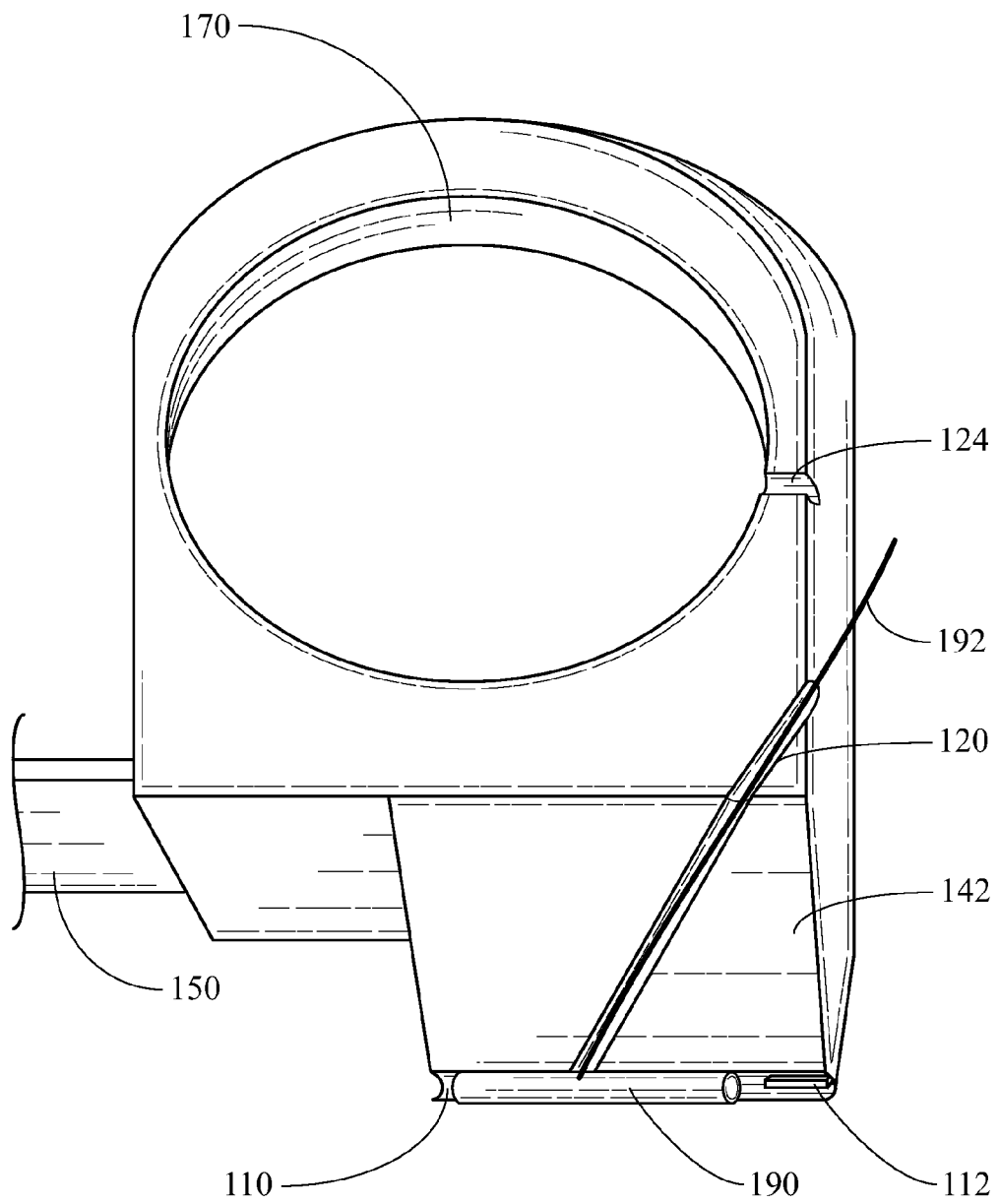
FIG. 2 is a close-up perspective view of an anchor receiving portion of the embodiment of FIG. 1 illustrating the placement of a suture anchor member and a suture on the anchor receiving portion.

The first portion 140 further includes a tapered protrusion 142 that extends away from the main body. The tapered protrusion 142 is shaped to mate with a needle receiving portion 130 disposed on the second portion 160. An anchor receiving portion 110 is disposed on an outer surface of the tapered protrusion 142, and is shaped to receive and restrain a suture anchor member 190 (shown in FIG. 2) against an outer surface thereof. The suture anchor member 190 is a substantially cylindrical member made from a stainless steel cannula or other biocompatible materials, and is coupled to a suture 192 at a longitudinal center thereof, thus resulting in a "T" shape. Accordingly, in one embodiment, the anchor member receiving portion 110 may be shaped as a slot having a substantially cylindrical shape with a diameter that is sized slightly larger than a diameter of the cylindrical T-anchor (FIGS. 1 and 2). A needle alignment member 112 may be disposed on the surface of the anchor member receiving portion 110 to aid in aligning the slot 183 cut into the distal tip of the needle 182 with the suture 192. The needle alignment member 112 protrudes perpendicularly outward from the surface of the anchor member receiving portion 110 and is shaped to engage the slot 183, as shown in FIG. 5b. For example, and without limitation, the needle alignment member 112 may be a raised tab or a ridge having a rectangular, triangular, or "U" shaped cross section. Other shapes capable of engaging and aligning the slot 183 in the needle 182 are contemplated.

A suture receiving portion 120 may be disposed at or near a longitudinal center of the anchor receiving portion 110. The suture receiving portion 120 may extend away from the anchor member receiving portion 110 and toward the operator interface feature 170 at an angle such that the suture receiving portion 120 and the anchor receiving portion 110 form a generally "T" shaped junction and are in mechanical communication with each other. The suture receiving portion 120 extends away from the anchor member receiving portion 110 at an oblique angle to accommodate the angled suture 192/suture anchor member connection, which typically ranges between 20° and 90°. In some embodiments, the suture anchor receiving portion 120 may angle away from the anchor member receiving portion 110 at any non-parallel (e.g. angles within a range greater than 0° and less than)180° angle as measured from a plane that is tangent to the trough of the slot-shaped anchor receiving portion 110. In other embodiments, the suture anchor receiving portion 120 angles away from the anchor member receiving portion 110 at less than or equal to about 90°, and may be angled away from the anchor member between about 45° and 80°.

The suture receiving portion 120 may have a slot shape, as shown in FIG. 1, or a slit shape, as shown in FIG. 1a. In embodiments having a slit shape, the suture receiving portion 120 may include a guide notch 121 to facilitate insertion of the suture 192 into the slit 120. The guide notch 121 may be disposed at the angular junction between the suture receiving portion 120 and the anchor receiving portion 110.

Figure 3:
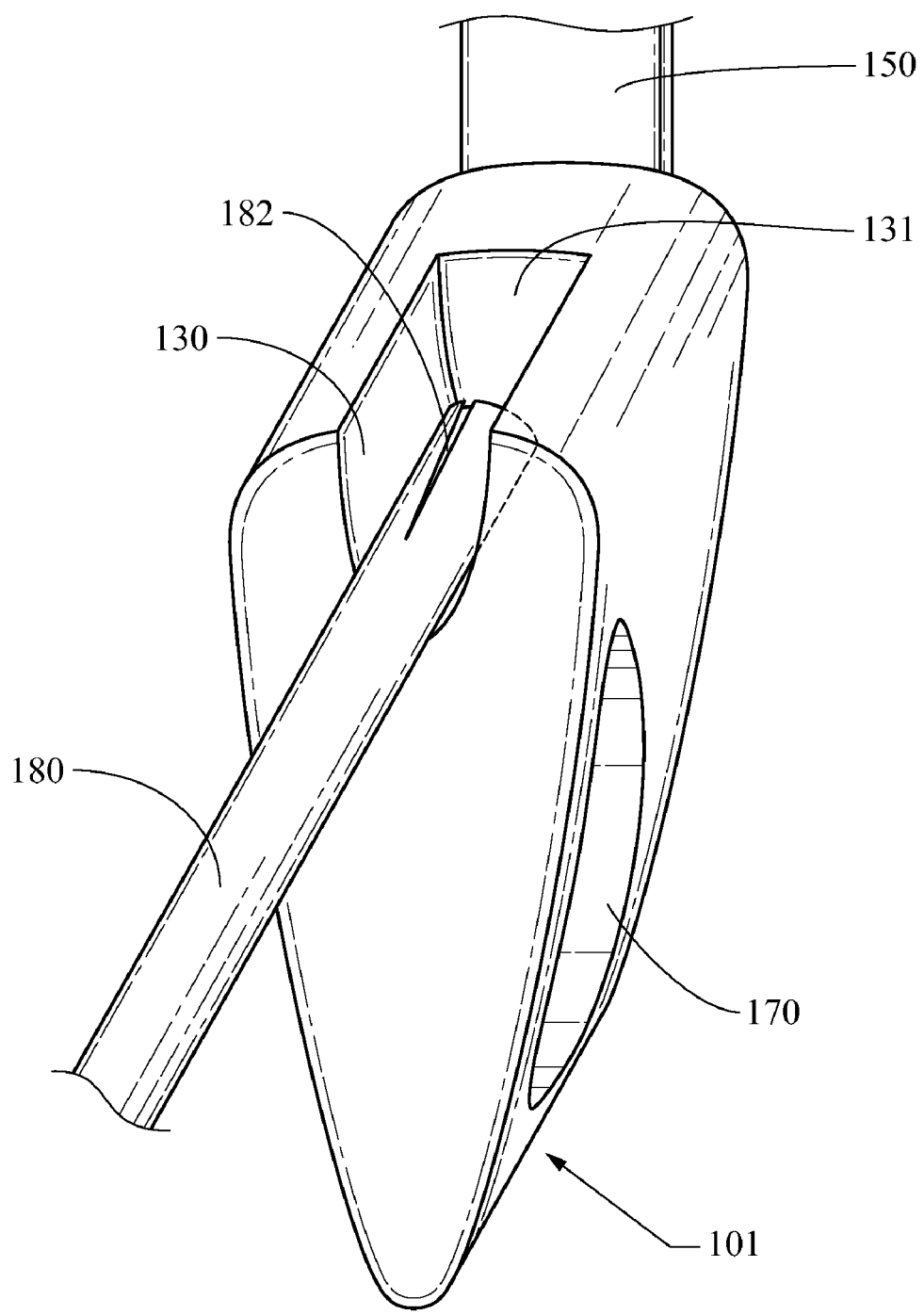
FIG. 3 is a close-up perspective view of a needle receiving portion of the embodiment of FIG. 1 illustrating the placement of a sheathed needle on the needle receiving portion.

Turning to FIG. 3, the second portion 160 of the body 101 includes a needle receiving portion 130. The needle receiving portion 130 is a slot having a "V" shaped profile that is sized and shaped to receive at least a portion of the tapered protrusion 142 of the first portion 140. A trough of the slot-shaped needle receiving portion 130 may have a rounded shape that is sized to roughly the diameter of the sheath 180. Like the first portion 140, the second portion 160 also includes an operator interface feature 170 in the form of an aperture that is sized to receive a human finger.

Figure 4:
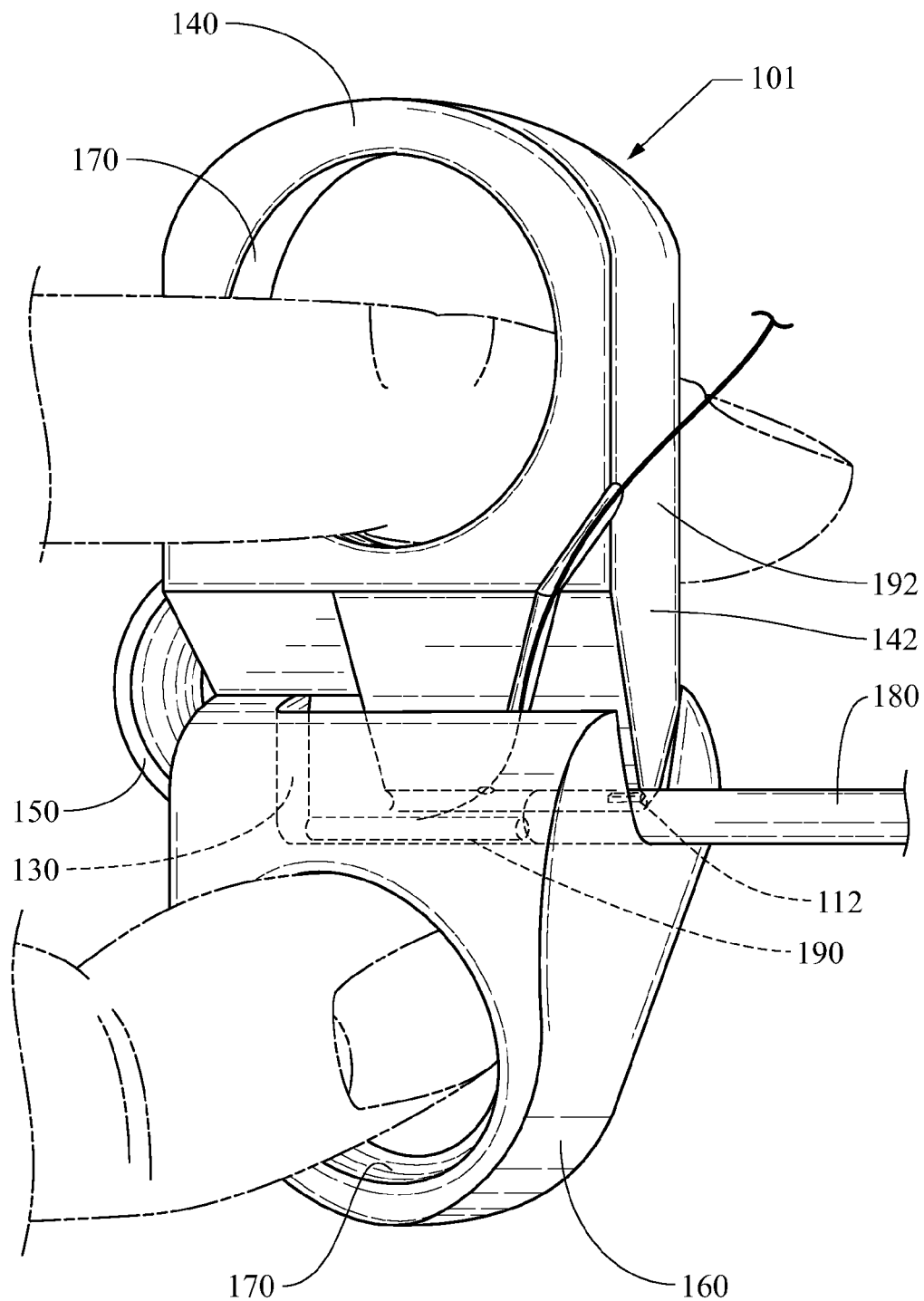
FIG. 4 is a perspective view of the embodiment of FIG. 1 in an anchor member insertion configuration.

The first and second portions are connected by a hinge member 150 that allows the suture anchor member loading device 100 to rotate between an initial configuration/position in which the first and second portions are rotationally offset, as shown in FIG. 1, to a loading configuration in which the tapered protrusion 142 of the first portion 140 is disposed within the needle receiving portion 130 of the second portion 160, as shown in FIG. 4. The hinge member 150 may be made of a flexible strip of material that is integrally formed with the first and second portions 140, 160 of the body 101. The hinge member 150 may be made from the same or different materials than the first or second portions 140,160 of the body 101. However, it should be understood that the hinge member 150 is not limited thereto, and may be attached to the first and second members 140, 160 by adhesive, mechanical fasteners, or the like. Further, non-flexing, mechanically articulating hinge members 150 are also contemplated, for example and without limitation, pin joints, ball joints, and socket joints.

In operation, the suture anchor member 190 is placed on the outer surface of the anchor receiving portion 110 and longitudinally positioned such that the suture 192 is aligned with the suture receiving portion 120 (FIG. 2). The suture is then positioned within the suture receiving portion 120 and tensioned, thereby causing the suture anchor member 190 to contact the walls of the anchor member receiving portion 110. Because the anchor member receiving portion 110 has a rounded slot shape that substantially mirrors the shape of the suture anchor member 190, the walls of the anchor receiving portion 110 prevent the suture anchor member 190 from rotational movement. Further, because the suture is tensioned, interference between the suture 192 and the walls of the suture receiving portion 120 prevent the anchor member 190 from translating longitudinally along the anchor member receiving portion 110. Thus, once the suture has been tensioned, movement of the suture anchor member 190 is restrained in all three degrees of freedom, as shown in FIG. 2. The suture is then held in tension by the operator, or inserted into the lock notch 124 to maintain the tensile force.

In embodiments where the suture receiving portion 120 is a slit, the suture 192 is initially placed on the guide notch 121 and then drawn downward into the slit under tension. As the suture 192 moves into the slit, the suture 192 forces opposing walls of the slit away from each other, thereby placing the suture 192 under compression and frictionally securing the suture 192 in place.

Once the suture 192 and suture anchor member 190 have been placed on the body 101, an operator inserts one finger, typically the index finger, into the operator interface feature 170 of the first portion 140, and inserts another finger, typically the thumb, into the operator interface feature 170 of the second portion 160. The operator then rotates the first portion 140 toward the second portion 160, which causes the hinge member 150 to flex. As the first and second portions 140, 160 move toward each other, the tapered protrusion 142 housing the anchor member receiving portion 110 and the suture anchor member 190 is inserted into the needle receiving portion 130 (FIG. 4). The walls of the needle receiving portion 130 contact and guide the tapered protrusion 142 such that the suture anchor member 190 is guided to, and disposed on or adjacent to the trough of the needle receiving portion 130, as shown in FIG. 4.

As shown in FIG. 3, the needle 182 is placed into the needle receiving portion 130 such that it rests in the bottom, trough portion of the slot, as shown in FIG. 2. The needle 182 may be placed in the needle receiving portion 130 in a retracted state in which the tip of the needle 182 is housed within a sheath 180 to prevent the operator from being exposed to the sharp tip of the needle 182. The sheath 180 may be placed on the needle receiving slot such that a distal end of the sheath is spaced away from the rear wall 131. The distal end of the sheath 180 may be placed outward of the needle alignment member 112 to allow the needle alignment member 112 to engage and align the needle 192 when it is advanced out of the sheath 180.

As shown in FIG. 5a, the needle 182 is then advanced out of the distal end of the sheath 180. Initially, the needle 182 contacts the needle alignment member 112, and the user rotates the needle until the slot 183 is aligned with the needle alignment member 112 and the suture 192. After the needle has been aligned, the operator advances the needle until it contacts an end of the anchor member 190. The operator then manipulates the needle 182 to seat an end portion of the anchor member 190 within a lumen of the needle 182. The needle 182 is then advanced until substantially the entirety of the suture anchor member 190 is housed within the needle lumen. Once the suture anchor member 190 has been loaded into the needle 182, the sheath 180 is advanced to cover the sharp tip of the needle 182, and the suture 192 is pulled into a slit in the sheath 180 to frictionally secure the suture 192 in place and prevent the suture anchor member 190 from inadvertently or prematurely exiting the needle 182.

Figure 6:
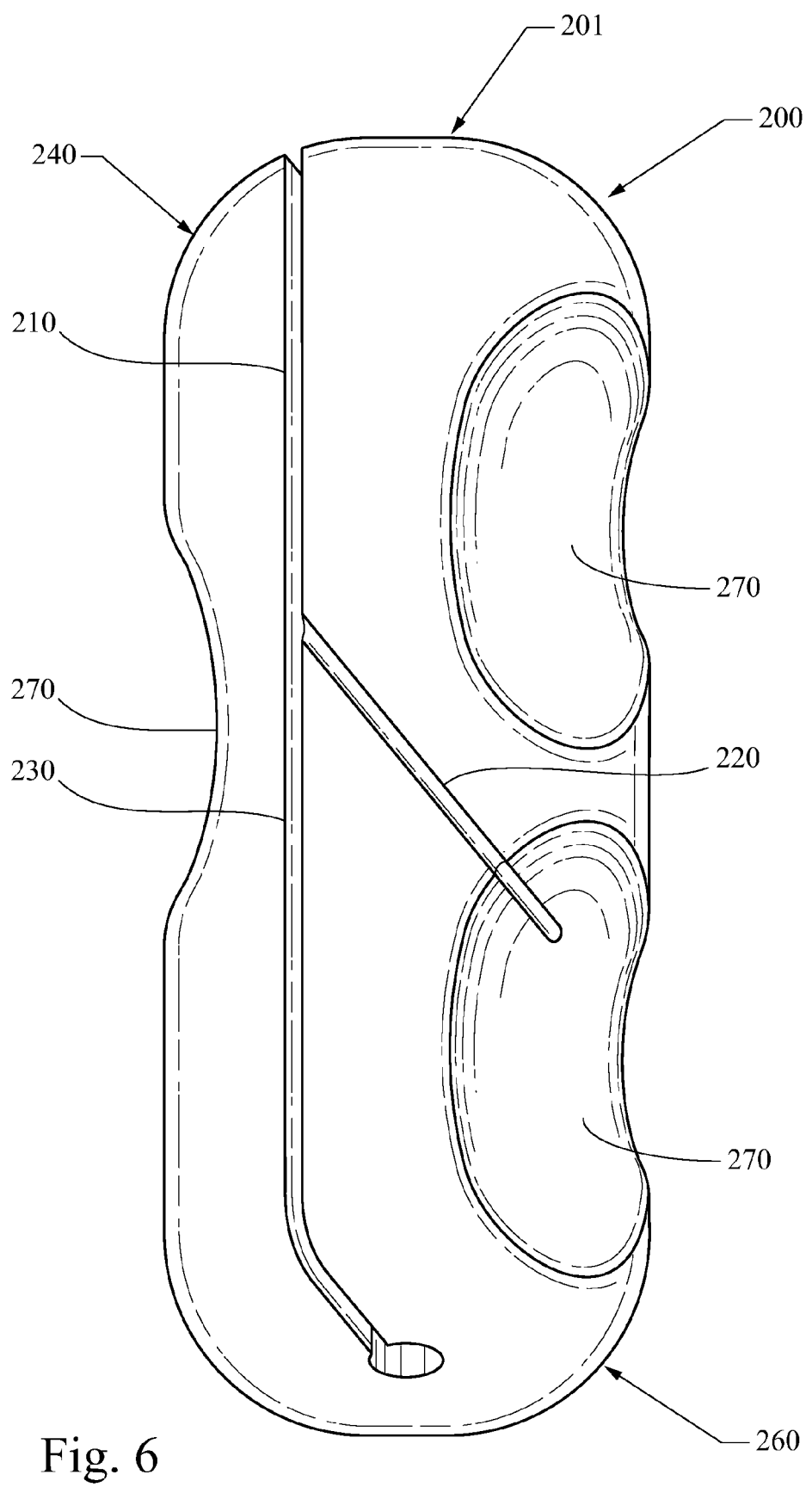
FIG. 6 is perspective view of another embodiment of a suture anchor member loading device.

FIG. 6 illustrates another embodiment of a suture anchor member loading device 200. The suture anchor member loading device 200 includes a body 201 having a first portion 240 and a second portion 260. The body 201 may have a unitary and monolithic "capsule" shaped structure including two operator interface features 270 disposed on one side, and one operator interface feature 270 disposed on the opposite side. The operator interface features 270 may be formed as concave depressions in the outer surface of the body 201 that are sized and shaped to receive human fingers.

Figure 7:
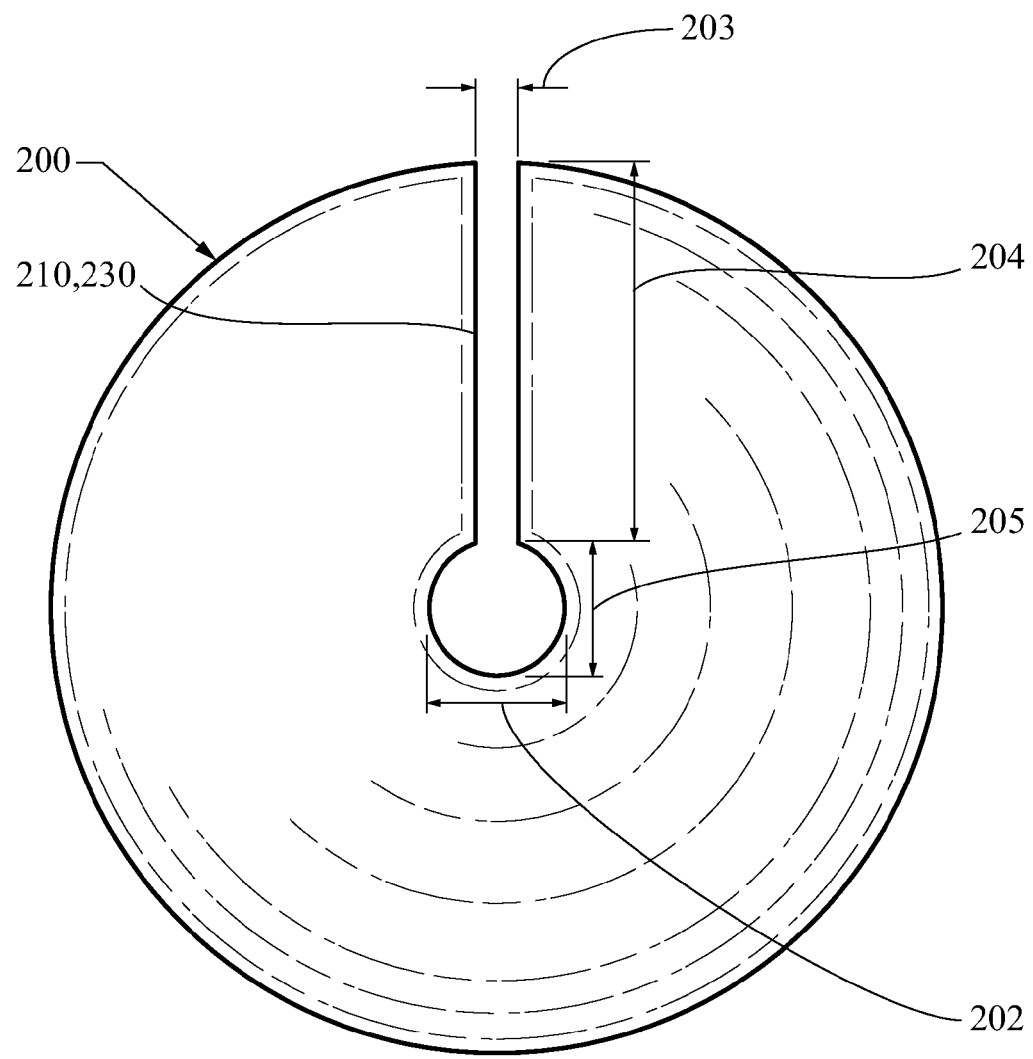
FIG. 7 is an end view of the embodiment of FIG. 6.
Figure 8:
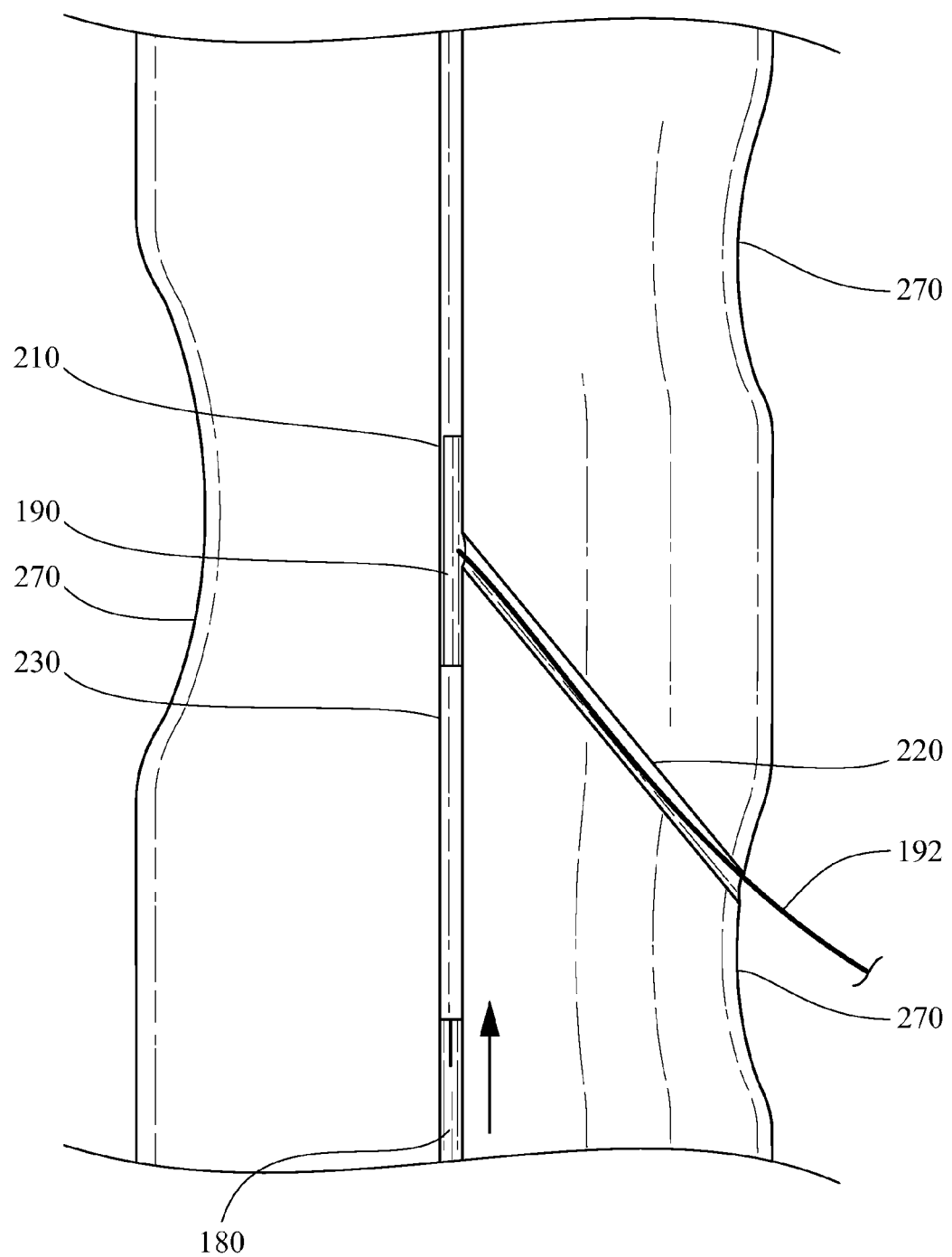
FIGS. 8-11 are top views of the embodiment of FIG. 6 illustrating the process of loading a suture anchor member into a sheathed needle.
Figure 9:
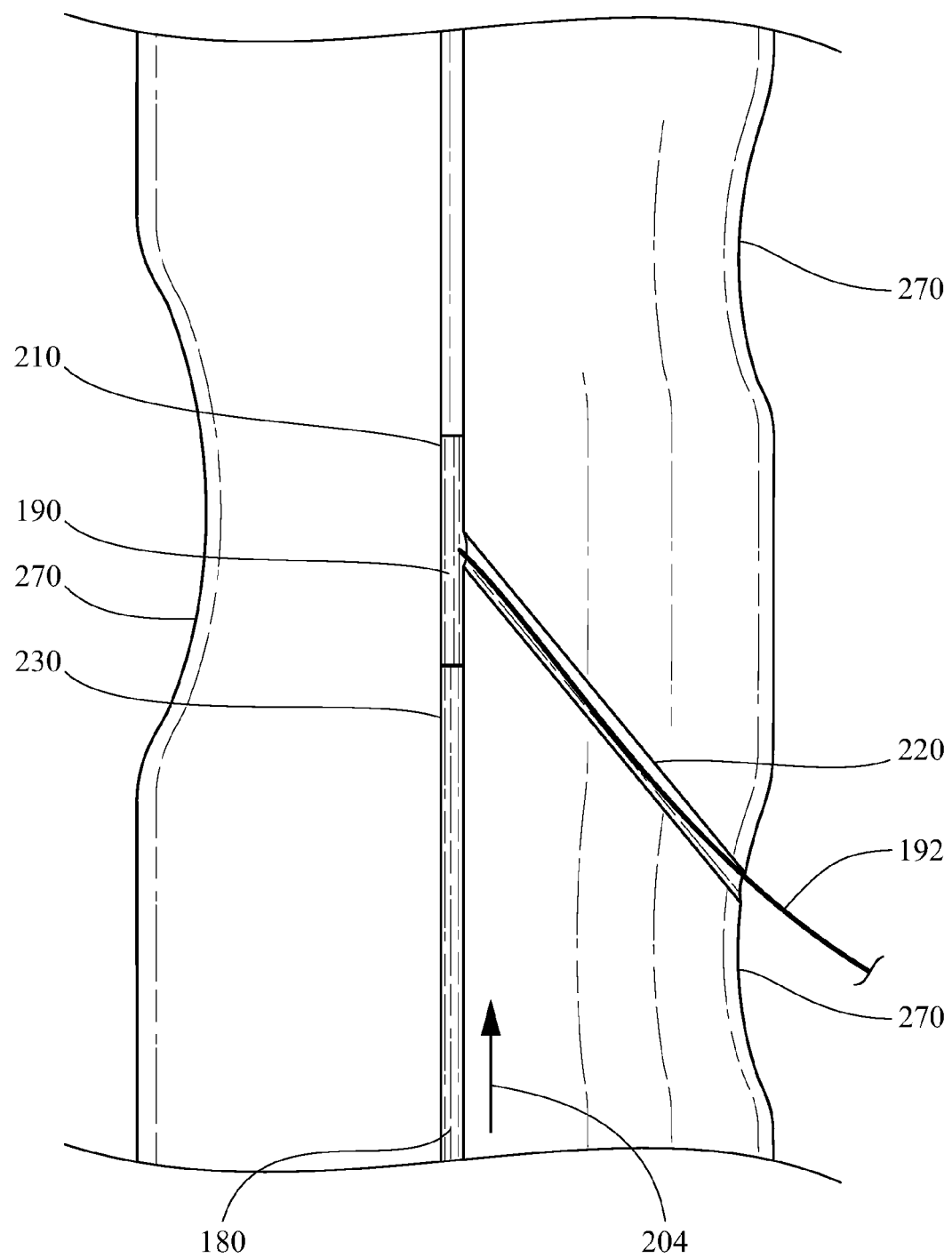
Figure 10:
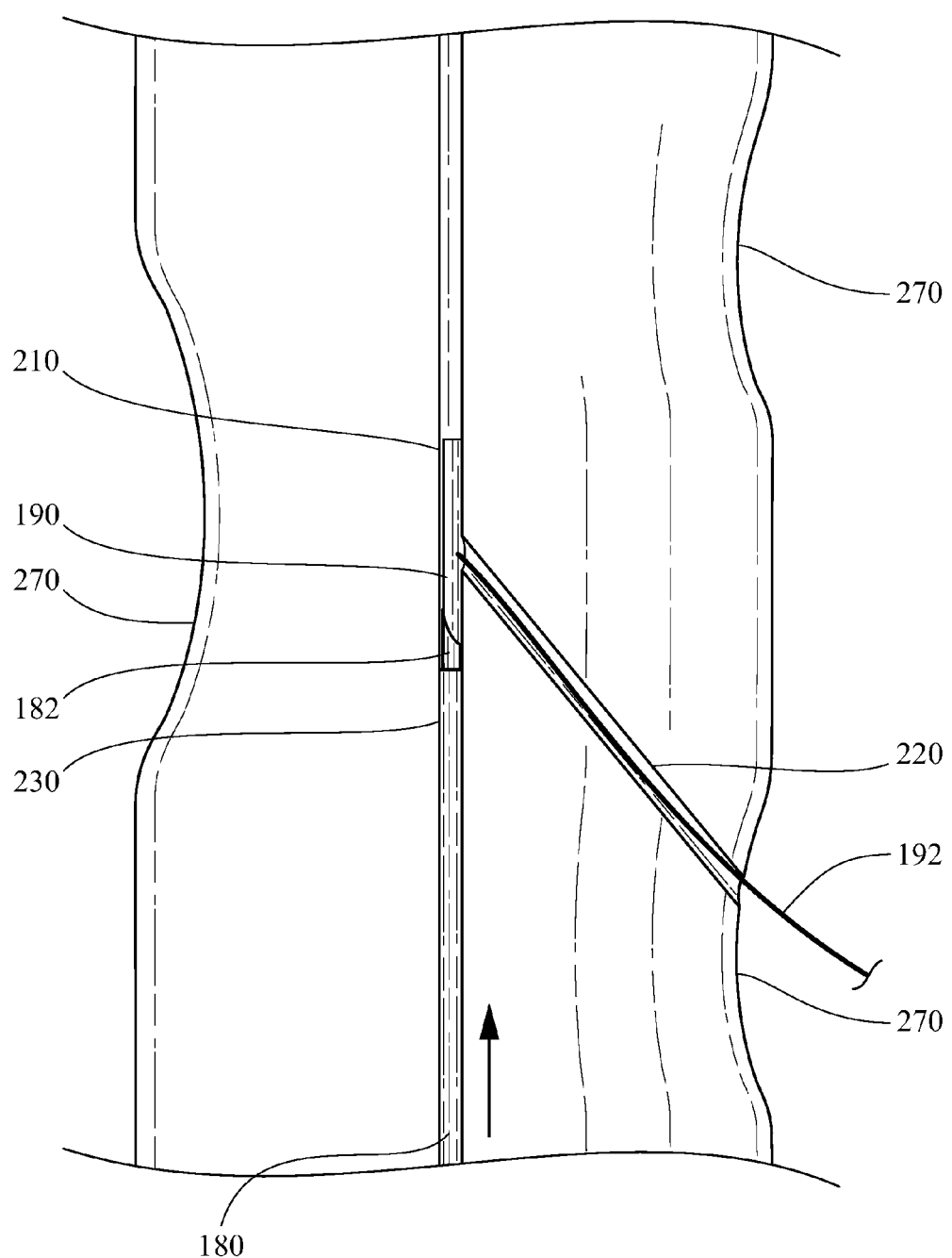
Figure 11:
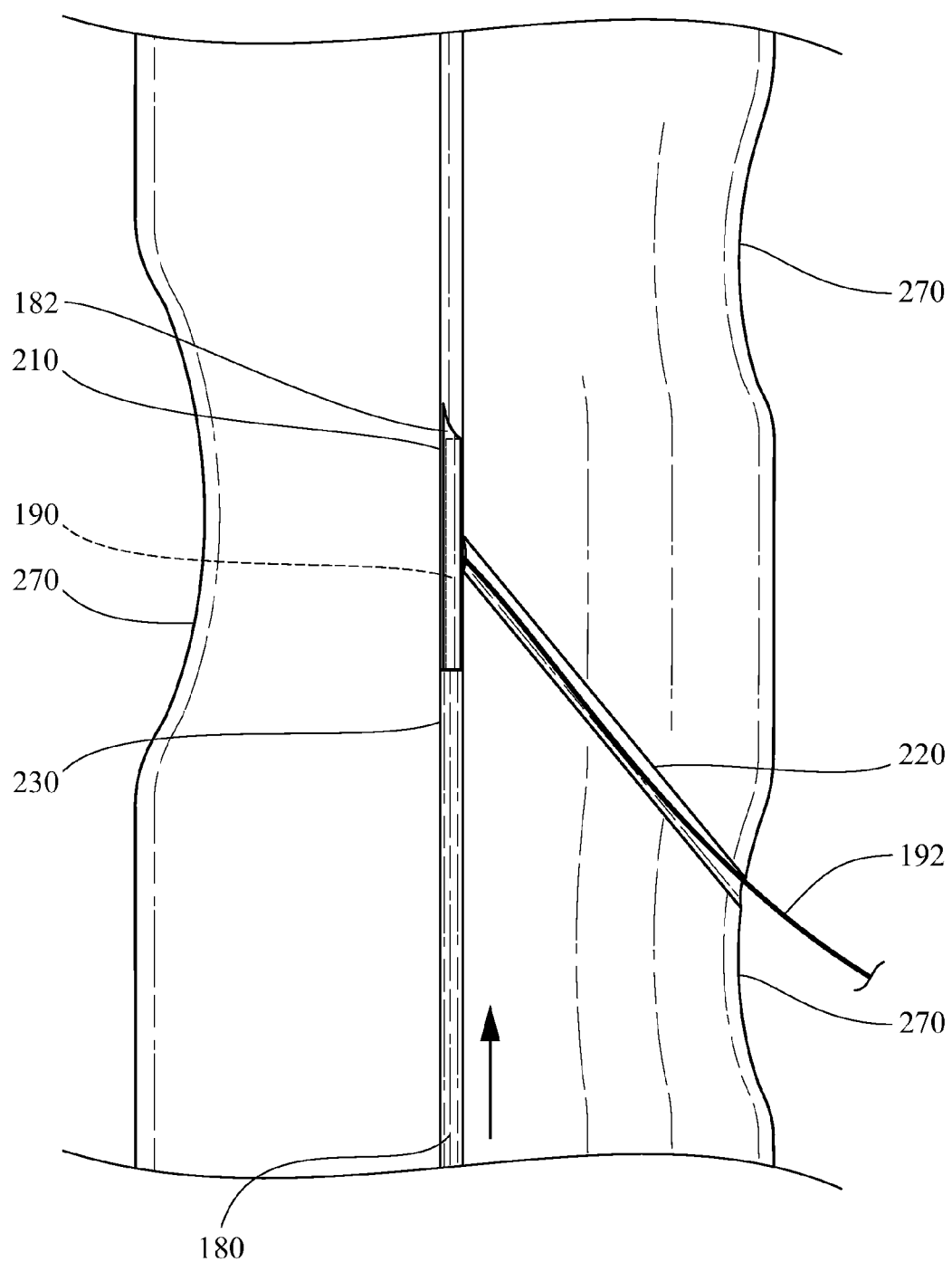

The first portion 240 includes an anchor receiving portion that is shaped to receive and restrain a suture anchor member 190 in contact with an outer surface thereof. In one embodiment, the anchor member receiving portion 210 may be a slot having an inner portion 205 disposed at the trough portion of the slot and an outer portion 204 disposed between the inner portion 205 and the outer surface of the body 201, as shown in FIG. 7. The inner portion 205 may have a substantially cylindrical cross section whose diameter is sized to be slightly larger than the diameter of the cylindrical "T" shaped suture anchor member 190 shown in FIG. 2, such that the inner portion 205 can simultaneously house the suture anchor member 190, the sheath 180 and the needle 182. The outer portion 204 of the slot may have a substantially rectangular cross section that extends from an upper edge of the cylindrical inner portion 205 of the slot to the outer surface of the body 201, thereby creating a single, continuous opening between the trough of the slot and the outer surface of the body 201. The outer portion 204 has a width that is narrower than the diameter of the inner portion 205 and the diameter of the suture anchor member 190, such that when the suture anchor member 190 is inserted into the cylindrical inner portion 205 of the slot, the suture anchor member 190 is restrained therein and cannot enter the rectangular outer portion 204. The inner portion 205 is disposed at a radial center of the body 201 and extends co-axially along the longitudinal, central axis of the body 201. That is, the central axis of the inner portion 205 and the body 201 may be substantially the same. The anchor member receiving portion 210 may be disposed such that it is circumferentially centered between the circumferentially opposing operator interface features 270.

As shown in FIG. 6, a suture receiving portion 220, may be disposed at or near a longitudinal center of the body 201 and extend away from the anchor member receiving portion 210 and toward the operator interface features 270 on either side of the body 201 at an angle such that the suture receiving portion 220 and the anchor receiving portion 210 form an angled "T" shaped junction. The suture receiving portion 220 extends away from the anchor member receiving portion 210 at an oblique angle. However, it should be understood that the angle is not limited thereto and may extend away at any non-parallel (e.g. angles between a range that is greater than 0° or less than 180°) angle as measured from a plane tangent to a wall of the outer portion 204 of the anchor receiving portion 210. An end of the suture receiving portion 220 is connected to a wall of the outer portion 204 of the anchor member receiving portion 210 such that the suture receiving portion 220 is in mechanical communication with the anchor receiving portion 210.

Figure 13:
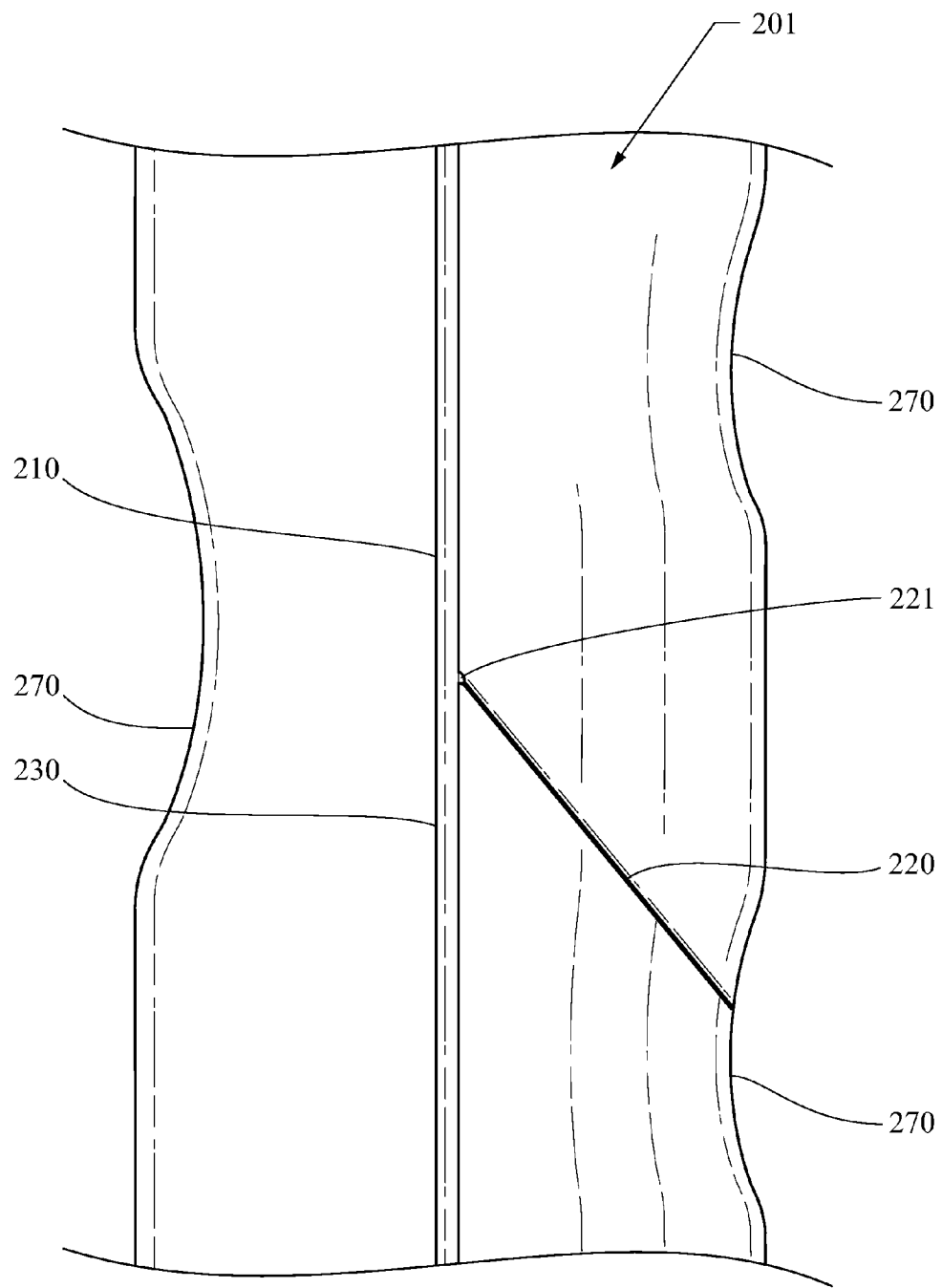
FIG. 13 is a top view of an alternative embodiment of FIG. 6.

The suture receiving portion 220 has a slot shape, as shown in FIGS. 6 and 8-11, or a slit shape, as shown in FIG. 13. In embodiments having a slit shape, the suture receiving portion 220 may include a guide notch 221 to facilitate insertion of the suture 192 into the suture receiving portion 220. The guide notch is disposed at the angled junction between the suture receiving portion 220 and the anchor receiving portion 210.

Returning to FIG. 6, the second portion 260 of the body 201 includes a needle receiving portion 230. In a one embodiment, the needle receiving portion 230 is a slot having the same shape and size as the anchor member receiving portion 210 shown in FIG. 7, such that the anchor member receiving portion 210 and the needle receiving portion 220 form a substantially continuous and uniformly shaped receiving structure extending from one longitudinal end of the body 201 to the other.

Referring to FIGS. 8-12, in operation, the suture anchor member 190 is inserted into either end of the anchor member/needle receiving portion 210, 230 such that the suture 192 is aligned with and extends through the outer portion 204. The suture anchor member 190 is then advanced through the anchor member/needle receiving portion 210, 230 by pulling the suture 192 until the point of connection between the suture 192 and the suture anchor member 190 is disposed at the longitudinal junction between the anchor receiving portion 210 and the suture receiving portion 220. The suture is then inserted into the suture receiving portion 220 and tensioned, thereby causing the suture anchor member 190 to contact the walls of the anchor member receiving portion 210. Because the anchor member receiving portion 210 has a cylindrical shape, the walls of the anchor receiving portion 210 prevent the suture anchor member 190 from rotating. Further, because the suture 192 is tensioned, the interference between the suture 192 and the walls of the suture receiving portion 220 prevent the anchor member 190 from translating longitudinally along the anchor member receiving portion 210. Thus, once the suture 192 has been tensioned, movement of the suture anchor member 190 is restrained in all three degrees of freedom. The suture 192 is then held in tension by the operator.

In embodiments where the suture receiving portion 220 is a slit, the suture 192 is initially placed on the guide notch 221 and then drawn downward into the slit under tension. As the suture 192 moves into the slit, the suture 192 forces opposing walls of the slit away from each other, thereby placing the suture 192 under compression and frictionally securing the suture 192 in place.

Figure 12:
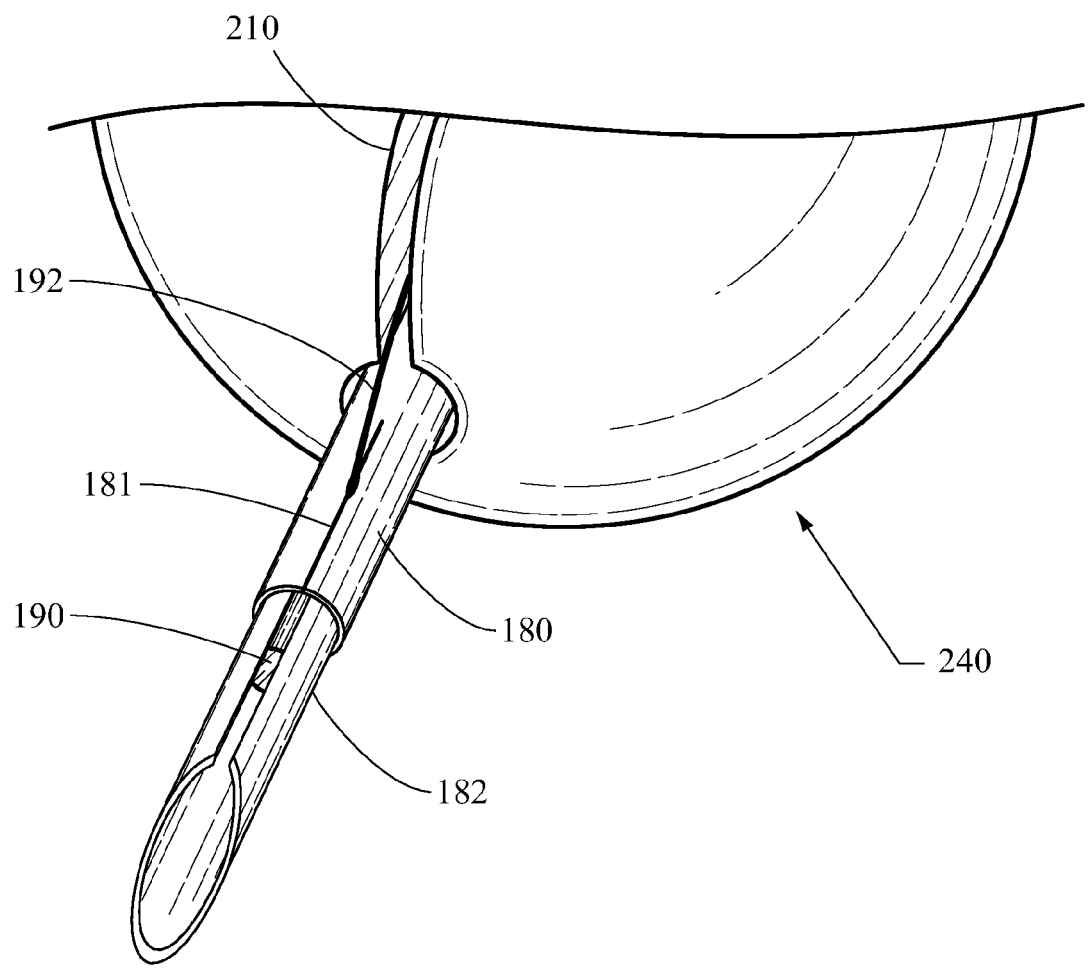
FIG. 12 is a close-up view of an end of the embodiment of FIG. 6 after the suture anchor member has been loaded into the needle.

Once the suture 192 and suture anchor member 190 have been placed on the body 201, an operator grasps the suture anchor loading device 200 by placing two fingers and a thumb in the depressions of the operator interface features 170. The needle 182 is inserted into the inner portion 205 of the needle receiving portion 230 and advanced until the distal end of the sheath 180 is adjacent an end of the suture anchor member 190. The needle 182 is inserted into the needle receiving portion 130 in a retracted state in which the tip of the needle 182 is housed within a sheath 180 to prevent the operator from being exposed to the sharp tip of the needle 182. The needle 182 is then advanced out of the distal end of the sheath 180 and the operator manipulates the needle 182 until the end of the suture anchor member 190 is disposed within the distal tip of the needle 182. The user then continues to advance the needle 182 until it contacts the suture 192 and rotates the needle as necessary until the slot 183 is aligned with the suture 192. After the needle 182 has been aligned, the operator advances the needle 182 until substantially the entirety of the suture anchor member 190 is housed within the needle lumen. Once the suture anchor member 190 has been loaded into the needle 182, the needle 182 may be advanced until the distal tip exits the end of the anchor receiving portion 210, as shown in FIG. 12. The sheath 180 is then advanced to cover the sharp tip of the needle 182, and the suture 192 is pulled into a slit in the sheath 180 to frictionally secure the suture 192 in place and prevent the suture anchor member 190 from inadvertently or prematurely exiting the needle 182.

One or more of the suture anchor member loading devices 100, 200 described above may be combined and distributed in a kit. In a one embodiment, the kit may include packaging that is shaped to safely, securely, and removably receive and restrain at least one suture anchor member loading device 100, 200, at least one delivery needle 182 housed within a sheath 180, and at least one suture 192 connected to a suture anchor member 190. In one embodiment, a suture anchor member 192 may be preloaded into the needle 182. In other embodiments, the kit may include a plurality of needles 182 of different types or sizes for different applications or multiple needles 182 of the same type/size for applications where reuse of the needle 182 is not possible or preferred. The kit may also include a plurality of suture/suture anchor members 190/192. In kits where the a suture anchor member 190 is not preloaded into the needle 182, the user may load the suture anchor member 190 into the suture anchor member loading device 100, 200 using the methods described above. In cases where the needle 182 is to be reused, the suture anchor members 192 may be successively loaded into the needle 182 using the suture anchor member loading device(s) 100, 200.

In the embodiments shown in the Figures, the suture 192 and the suture anchor member 190 are preferably loaded into the suture anchor member loading devices such that the suture angles back along the needle into which it will be inserted. Loading the suture 192 and the suture anchor member 190 in this way may prevent the suture 192 from buckling and may prevent the needle or the anchor member 190 from cutting or otherwise damaging the suture 192 when the suture is bent over itself to interface with the slit in the catheter 185.

While preferred embodiments of the invention have been described, it should be understood that the invention is not so limited, and modifications may be made without departing from the invention. The scope of the invention is defined by the appended claims, and all devices that come within the meaning of the claims, either literally or by equivalence, are intended to be embraced therein. Furthermore, the advantages described above are not necessarily the only advantages of the invention, and it is not necessarily expected that all of the described advantages will be achieved with every embodiment of the invention.

I claim:

1. A suture anchor member loading device, comprising:
an anchor loading body having first and second portions shaped to prevent operator contact with a tip of a needle when manually loading a suture anchor member into a lumen of the needle;
an anchor receiving portion disposed in the first portion of the body, the anchor receiving portion being shaped to receive and restrain the suture anchor member;
a suture receiving portion disposed in the first portion of the body, the suture receiving portion extending from a first end in mechanical communication with the anchor receiving portion and a second end disposed on an outer surface of the body, the suture receiving portion extending away from the anchor receiving portion at an angle, wherein the suture receiving portion is shaped to receive a suture connected to the suture anchor member such that when the suture is tensioned the suture anchor member is translationally and rotationally restrained within the anchor receiving portion;
a needle receiving portion disposed in the second portion of the body, wherein the needle receiving portion is shaped to slidably receive and guide the needle such that the suture anchor member is received into the lumen of the needle when the needle is slidably advanced through the needle receiving portion, wherein the first portion of the body and the second portion of the body are movably connected to each other, the body having a first configuration wherein the first and second portions are displaced from each other and a second configuration wherein the first and second portions are disposed adjacent each other such that the anchor receiving portion is disposed adjacent the needle receiving portion thereby allowing the suture anchor member to be inserted into the lumen of the needle when the needle is slidably advanced through the needle receiving portion.

2. The device of claim 1, wherein the anchor receiving portion is a slot extending from the outer surface of the body toward a center portion of the first portion of the anchor loading body.

3. The device of claim 1, wherein the suture receiving portion is a slot extending from the outer surface of the body toward a center of the body.

4. The device of claim 1, wherein the suture receiving portion is a slit extending from the outer surface of the body toward a center of the body, the slit having opposing portions which engage each other when no suture is disposed within the slit, and which engage and frictionally secure the suture when the suture is disposed within the slit and between the opposing portions.

5. The device of claim 1, wherein the needle receiving portion and the anchor receiving portion are substantially coaxial.

6. The device of claim 5, wherein the anchor member receiving portion is a slot extending from an outer surface of the first portion of the body toward a center portion thereof.

7. The device of claim 5, wherein the needle receiving portion is a slot having an open end and a closed end, the slot extending from an outer surface of the first portion of the body toward a center portion thereof.

8. The device of claim 1, wherein the first and second portions of the body are connected by a hinge, and wherein the anchor receiving portion forms a portion of an outer surface of the needle receiving portion when the first and second body portions are in the second configuration.

9. The device of claim 1, wherein the anchor receiving portion comprises a needle alignment member that protrudes away from an outer surface thereof, the needle alignment member being shaped to engage and align the needle when the needle is advanced through the needle receiving section.

10. The device of claim 9, wherein the anchor receiving portion is a slot extending from an outer surface of the first portion of the body toward a center portion thereof, and wherein the needle receiving portion is a slot extending from an outer surface toward a center of the second portion of the body.

11. The device of claim 1, wherein the hinge member is a flexible member integrally formed with the first portion at a first end and with the second portion at a second end.

12. The device of claim 11, wherein the suture receiving portion is a slit extending from the outer surface of the body toward a center of the first portion of the body, the slit having opposing portions which engage each other when no suture is disposed within the slit, and which engage and frictionally secure the suture when the suture is disposed within the slit and between the opposing portions.

13. The device of claim 1, in combination with: a suture anchor member attached to a first end of a suture, the suture anchor member being disposed in the anchor receiving portion; and a delivery needle comprising a sharp distal end, a lumen extending along a central axis of the needle, the lumen sized to slidably receive the suture anchor member, and a slot disposed at the sharp distal end, the slot extending proximally from a distal portion of the sharp distal end, wherein the slot is shaped to receive a portion of the suture, the delivery needle being disposed in the needle receiving portion.

14. A kit comprising:
a suture anchor member loading device comprising; an anchor loading body having first and second portions shaped to prevent operator contact with a tip of a needle when manually loading a suture anchor member into a lumen of the needle;
an anchor receiving portion disposed in the first portion of the body, the anchor receiving portion being shaped to receive and restrain the suture anchor member; and
a suture receiving portion disposed in the first portion of the body, the suture receiving portion extending from a first end in mechanical communication with the anchor receiving portion and a second end disposed on an outer surface of the body, the suture receiving portion extending away from the anchor receiving portion at an angle, wherein the suture receiving portion is shaped to receive a suture connected to the suture anchor member such that when the suture is tensioned the suture anchor member is translationally and rotationally restrained within the anchor receiving portion; a needle receiving portion disposed in the second portion of the body, wherein the needle receiving portion is shaped to slidably receive and guide the needle such that the suture anchor member is received into the lumen of the needle when the needle is slidably advanced through the needle receiving portion; a suture anchor member attached to a first end of a suture; a delivery needle comprising a sharp distal end, a lumen extending along a central axis of the needle, the lumen sized to slidably receive the suture anchor member, and a slot disposed at the sharp distal end, the slot extending proximally from a distal portion of the sharp distal end, wherein the slot is shaped to receive a portion of the suture; a sheath comprising a lumen sized to slidably receive the delivery needle, and a slit disposed at a distal end of the sheath, the slit defining opposing portions which engage each other when no suture is disposed within the slit, and which engage and frictionally secure the suture when the suture is disposed within the slit and between the opposing portions; and packaging, wherein the suture anchor member loading device, the suture anchor member, the delivery needle and the sheath are removably disposed within the packaging.

15. The Kit of claim 14, wherein the anchor receiving portion is a slot extending from an outer surface of the first portion of the body toward a center portion thereof, wherein the anchor receiving slot has a first width at an outer portion thereof and a second width at an inner portion thereof, the second width being greater than the first width.

16. The Kit of claim 14, wherein the needle receiving portion is a slot having an open end and a closed end, the slot extending from an outer surface of the first portion of the body toward a center portion thereof wherein the needle receiving slot has a first width at an outer portion thereof and a second width at an inner portion thereof, the second width being greater than the first width.

17. The Kit of claim 14, wherein the anchor receiving portion is a slot extending from an outer surface of the first portion of the body toward a center portion thereof, the anchor receiving slot having a first width at an outer portion thereof, and a second width at an inner portion thereof, the second width being greater than the first width, wherein the anchor receiving portion is in communication with the needle receiving portion, and wherein the first and second widths of the anchor receiving slot are substantially the same as the first and second widths of the needle receiving slot, respectively, such that the anchor receiving slot and the needle receiving slot form a single substantially continuous slot having substantially the same shape.

* * * * *